United States Patent
Tu Xuan et al.

[11] Patent Number: 5,429,889
[45] Date of Patent: Jul. 4, 1995

[54] MEASUREMENT APPARATUS AND PROCESS FOR SORTING USED BATTERIES AND ACCUMULATORS

[75] Inventors: Mai Tu Xuan, Ecublens; Thinh T. Nguyen, Onex; Jean P. Wiax, Croixde-Rozon; Michel Schwab, Bienne, all of Switerland

[73] Assignees: Titalyse SA, Meyrin; Detra SA, Bienne, both of Switzerland

[21] Appl. No.: 927,287
[22] PCT Filed: Mar. 27, 1991
[86] PCT No.: PCT/EP91/00617
 § 371 Date: Sep. 25, 1992
 § 102(e) Date: Sep. 25, 1992
[87] PCT Pub. No.: WO91/15036
 PCT Pub. Date: Oct. 3, 1991

[30] Foreign Application Priority Data
Mar. 27, 1990 [EP] European Pat. Off. ............ 90810247

[51] Int. Cl.⁶ ............................................. G07D 3/16
[52] U.S. Cl. ............................... 429/90; 324/239
[58] Field of Search ........................ 324/239; 429/90

[56] References Cited
U.S. PATENT DOCUMENTS

| | | | |
|---|---|---|---|
| 3,164,993 | 1/1965 | Schmidt | 324/239 |
| 3,265,964 | 8/1966 | Hunsaker | 324/239 |
| 3,281,668 | 10/1966 | Rosner et al. | 324/239 |
| 3,359,494 | 12/1967 | Anderson et al. | 324/239 |
| 3,665,298 | 5/1972 | Geiger | 324/41 |
| 4,663,112 | 5/1987 | Gradel et al. | 376/245 |
| 4,963,118 | 10/1990 | Gunn et al. | 453/3 |
| 5,119,023 | 6/1992 | Lloyd | 324/239 |

FOREIGN PATENT DOCUMENTS

| | | |
|---|---|---|
| 0123089 | 10/1984 | European Pat. Off. . |
| 7507009 | 11/1975 | France . |
| 1458792 | 12/1976 | United Kingdom . |
| 2108672 | 5/1983 | United Kingdom . |
| 2130728 | 6/1984 | United Kingdom . |

*Primary Examiner*—Mukund J. Shah
*Assistant Examiner*—Matthew V. Grumbling
*Attorney, Agent, or Firm*—Sandler Greenblum & Bernstein

[57] ABSTRACT

Apparatus and process for sorting used batteries and accumulators on the basis of their chemical constitution based on the analysis of the inductive effect produced by the substances which are contained in the battery or accumulator, and whose ferromagnetic properties differ according to their chemical constitution. The measurement process in which the apparatus is used is based on the consecutive application to the excitation circuit of at least two different voltage amplitudes at the same frequency or two different frequencies at the same voltage amplitude.

13 Claims, 3 Drawing Sheets

MEASUREMENT APPARATUS AND PROCESS FOR SORTING USED BATTERIES AND ACCUMULATORS

BACKGROUND OF THE INVENTION

Due to their convenience of use, and also due to the increasing use of portable electrical and electronic apparatus, so-called rechargeable batteries or accumulators have become an established part of everyday domestic life.

These batteries or accumulators are devices for storing chemical energy and converting the chemical energy into electrical energy. Taking into account that their chemical content is rich in heavy metals, at the end of their life these batteries and accumulators have the disadvantage in that they are undesirable in urban garbage and a special treatment is required to remove all of the toxic elements.

Processes envisaged in the field of treatment of used batteries and accumulators must be able to deal with three characteristic aspects of the problem:

Quantitative aspect: the battery/accumulator market is in constant expansion. Today, it is estimated that it is necessary to treat 100 tons of batteries and accumulators per year per million population. One ton of batteries or accumulators represents on average 20,000 to 22,000 units. This treatment capacity should be increased by a factor of 3 by the year 2000.

Qualitative aspect: the complexity of the chemical aspect of the treatment problem can be appreciated from the below-indicated tabulation of the amounts of heavy metals for different batteries and accumulators of the usual types:

| Type | Zn % | MnO$_2$ % | Hg % | Pb % | Cd % | Ag % | Ni % |
|---|---|---|---|---|---|---|---|
| Zinc-Carbon | 17 | 29 | 0.01 | 0.1 | 0.015 | — | — |
| Alkaline | 14 | 22 | 0.3 | 0.05 | — | — | — |
| Mercury Batteries | 11 | — | 33 | — | — | — | — |
| Silver Batteries | 10 | — | 1 | — | — | 10 | — |
| Zn-Air Batteries | 30 | — | 1 | — | — | — | — |
| Ni—Cd Accu. | — | — | — | — | 15 | — | 30 |

Zinc-carbon and alkaline batteries account for 97% of today's market, and Ni—Cd accumulators vary from 0.5 to 2%. But the latter are expected to increase up to 5% in 3 to 5 years.

Purity aspect: a method of treating used batteries and accumulators is only technically and economically feasible if the resulting products can be recycled as primary products. The value of these recycled products is directly related to their degree of purity.

Different processes for treating used batteries and accumulators have been developed. The technology employed is either the thermic route, or the non-dry route by means of electrolysis. However, for both of these technologies, the minimum purity of the recycled products can only be reached in the absence of foreign elements, or in the presence of a minimal quantity thereof. For instance, thermic or electrolytic processes developed for recycling Ni—Cd accumulators can tolerate only 1% of zinc-based elements (alkaline or zinc-carbon batteries). In the other case, the thermic process used for alkaline or zinc-carbon batteries can tolerate only less than 1% of cadmium batteries.

The treatment of used batteries or accumulators from the public at large involves the problem that it is difficult or even impossible to envisage a selective collection according to the nature of the batteries or accumulators. A method of sorting these collected batteries or accumulators is thus becoming a vital necessity for the subsequent treatment processes.

SUMMARY OF THE INVENTION

The present invention concerns a device and a process for analyzing used batteries and accumulators to enable them to be sorted according to their chemical composition. The device and process according to this invention enable used batteries and accumulators to be sorted in a rapid, safe and economical way, whatever may be their state and their composition.

There are several possibilities for determining the chemical composition of a used battery or accumulator, for example measurement of the specific mass. Specifically, a zinc-carbon battery has a specific mass of about 19 g/cm$^3$, an alkaline battery (Zn—MnO$_2$) about 3.0 g/cm$^3$ and a Ni—Cd accumulator about 3.6 g/cm$^3$. Unfortunately, this difference of specific mass is defined much less well in practice than in theory, and in some cases these values are completely inverted. When a used battery or accumulator is stored in an unprotected place for a long period of time, its specific mass may vary within large limits because of problems of absorption of humidity, leakage of electrolyte or corrosion. Consequently, measurement of the specific mass of a battery or accumulator is not a reliable way of determining its chemical composition.

The constitution of a battery or accumulator can also be determined by analyzing the nature of the elements contained inside. Such analysis is possible by the X-ray fluorescence method. This process is quite reliable but expensive, and requires a relatively long measuring time, which makes it economically non-feasible.

To remedy the aforementioned disadvantages, the present invention proposes a device and a process for determining the constitution of used batteries and accumulators based on analysis of the ferromagnetic properties of the elements contained in the battery or accumulator.

BRIEF DESCRIPTION OF THE DRAWINGS

The invention will be better understood by reading the following description, with reference to the accompanying drawings, in which.

DETAILED DESCRIPTION OF THE PREFERRED EMBODIMENTS

Figure 1A:
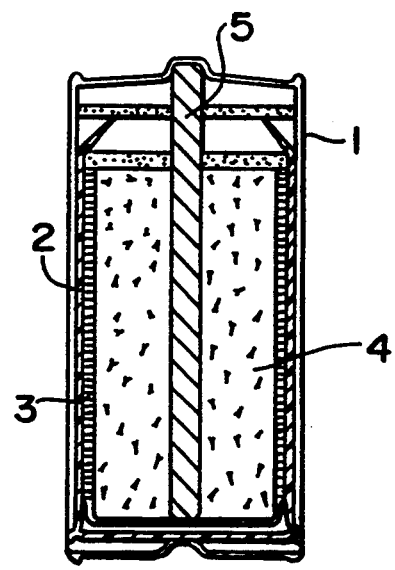
FIGS. 1a, 1b and 1c are cross-sections of a zinc-carbon battery, an alkaline battery and a Ni—Cd accumulator.

FIG. 1a shows a cross section of an zinc-carbon battery showing an envelope 1 of steel, plastic material or paper, an anode 2 of zinc, a separator 3 of porous plastic material, a cathodic mass 4 formed of a mixture of powders of manganese oxide and carbon with an electrolyte, and a cathodic current collector 5 made of graphite.

Figure 1B:
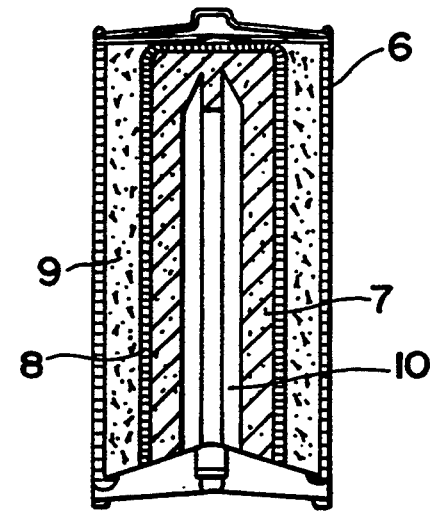

FIG. 1b shows a cross-section of an alkaline battery showing an envelope 6 of steel, an anodic mass 7 made of a mixture of zinc powder with an electrolyte, a separator 8 of porous plastic material, a cathodic mass 9 formed of a mixture of powders of manganese oxide and carbon with an electrolyte, and an anodic current collector 10 made of bronze.

Figure 1C:
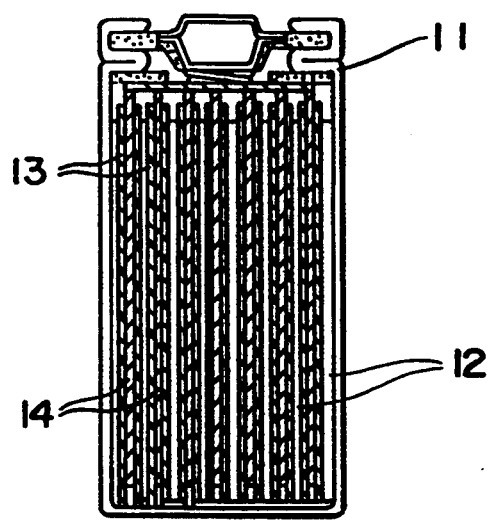

FIG. 1c shows a cross-section of a Ni—Cd accumulator showing an envelope 11 of nickel steel, anodes 12 formed of rolled cadmium foils, separators 13 of porous plastic materials, and cathodes 14 formed of nickel foils impregnated with a mixture of powders of nickel oxide and an electrolyte.

It can easily be seen that the contents of zinc-based batteries (zinc-carbon and alkaline batteries) are constituted of so-called non-ferromagnetic elements. In the case of a Ni—Cd accumulator, the ferromagnetic property of the contents is due to the presence of nickel-based components. Therefore, taking into account also the mass of the steel envelope, the ferromagnetic mass of zinc-based batteries is very different to that of Ni—Cd accumulators.

Figure 2:
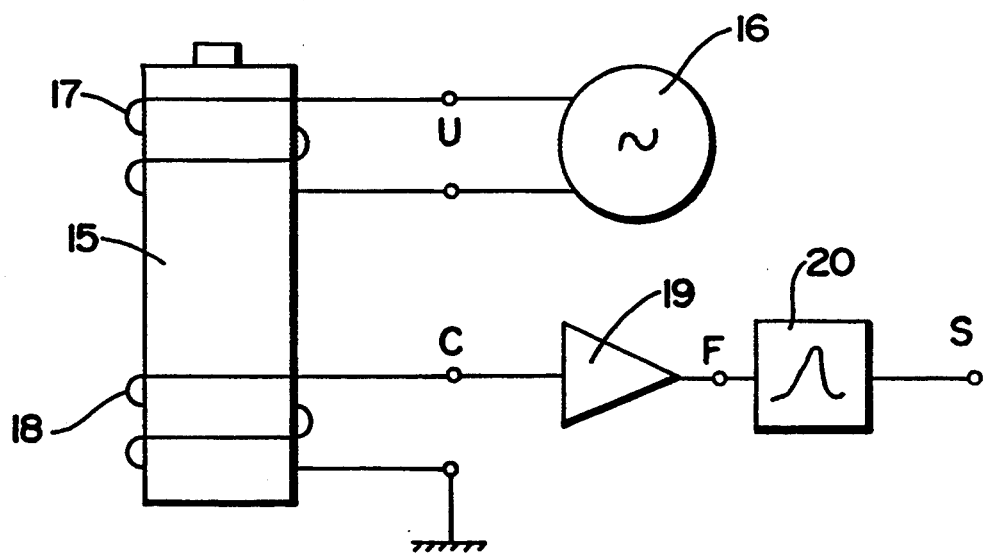
FIG. 2 shows the measuring device according to the invention.

FIG. 2 schematically shows an example of an embodiment of the measuring device according to the invention. An excitation circuit 17, supplied by a variable voltage source 16 supplying a voltage U, produces a variable flux passing through the mass of the battery or accumulator 15 to be analyzed. This variable flux is detected by an inductive sensor 18 connected to a processor (treatment means) 19, 20° The processor 19 is composed of one or more voltage amplifiers enabling the value of the voltage C at the output of the inductive sensor to be adapted to the input voltage F of the processor 20. The processor 20 is composed of one or more active or passive filters for suppressing undesired interference emanating from the sensor 18.

This measuring device supplies, at the output of the processor, a signal S whose amplitude is a function of the ferromagnetic mass of the battery or accumulator 15 to be analyzed. Analysis of the amplitude of signal S thus enables determination of the chemical composition of the battery or accumulator to be analyzed. It is clear that the voltage of signal S may be codified by a computer program to be used for controlling an electro-pneumatic or electro-mechanical device, not shown, for separating the batteries or accumulators according to their constitution in dependence on signal S.

Figure 3:
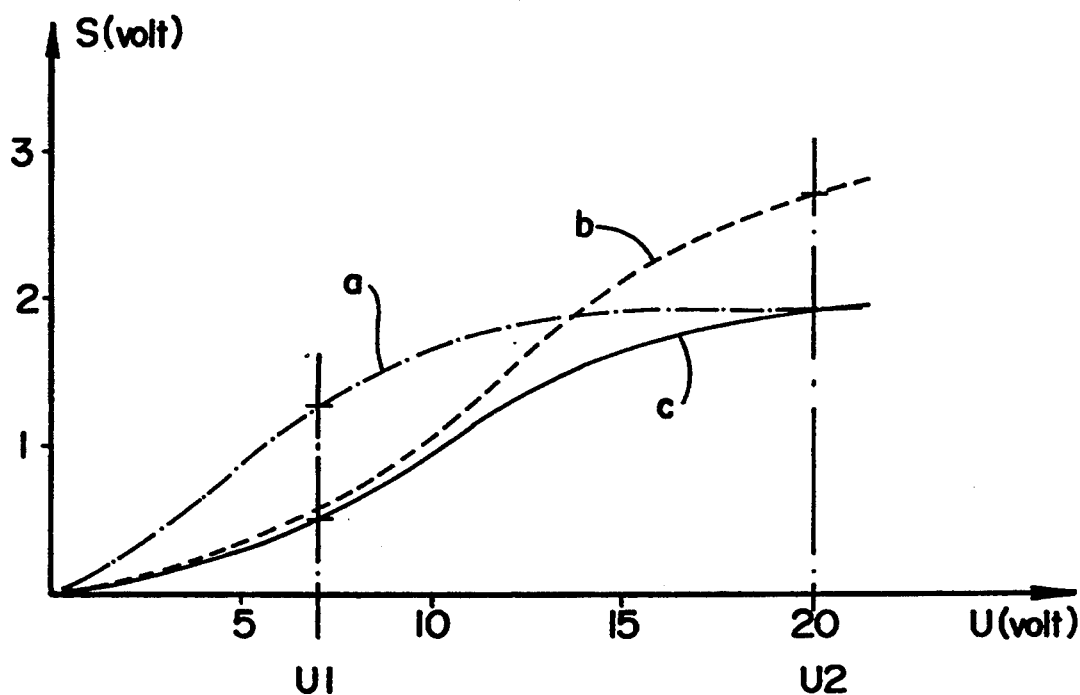
FIG. 3 shows electrical voltage response curves of the measuring device of FIG. 2.

FIG. 3 shows an example of the amplitude of signal S as a function of the amplitude of the supply voltage U of excitation circuit 17.

In this figure, curve a represents the response S of a first alkaline battery (Zn—MnO$_2$), curve b that of a second alkaline battery of different brand, and curve c the response of a Ni—Cd accumulator.

By applying an excitation voltage U1 of the order of 7 volts, the response S enables the first alkaline battery to be easily distinguished from the Ni—Cd accumulator. However, to distinguish the second alkaline battery from the Ni—Cd accumulator, it is necessary to apply an excitation voltage U2 of the order of 20 volts. In such a case, the analysis provides a reliable result only if the measuring device can apply two different voltage values to the excitation circuit 17.

Figure 4:
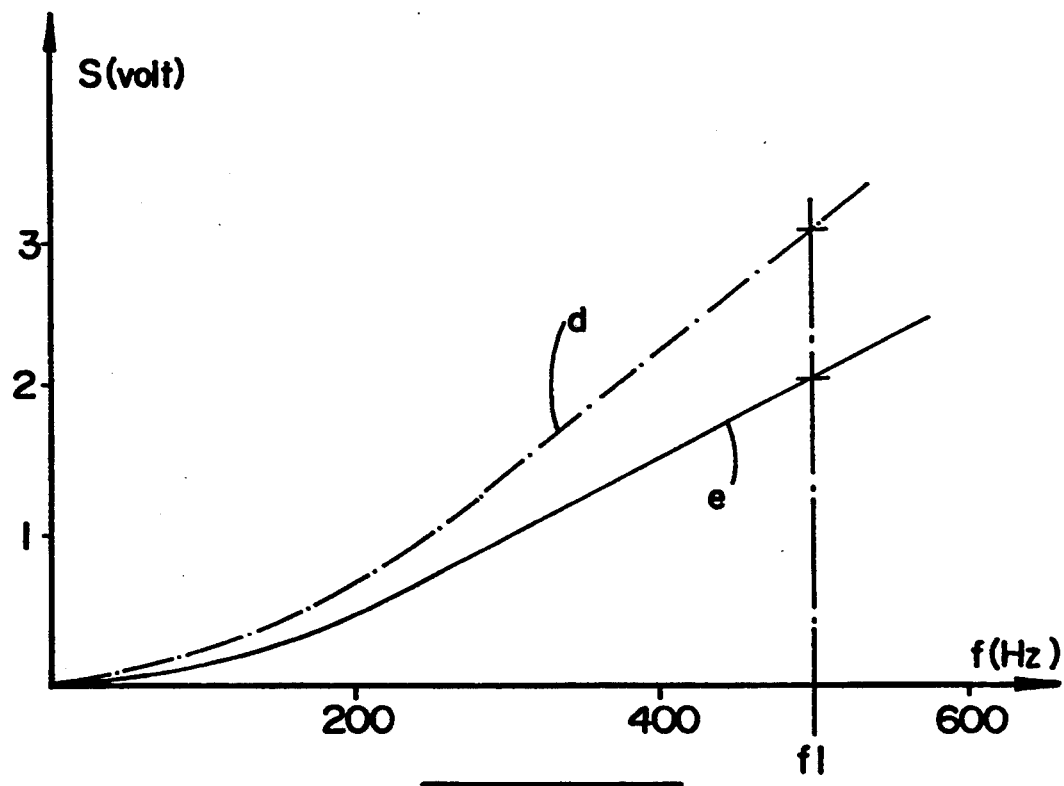
FIG. 4 shows frequency response curves of the measuring device of FIG. 2.

FIG. 4 shows the variation of the amplitude of signal S as a function of the frequency f of the excitation voltage U applied to circuit 17; in this case, the excitation voltage U is maintained constant at 10 volts.

In this figure, curve d represents the response S of an alkaline battery and curve e that of a Ni—Cd accumulator. It is noted that the alkaline battery can be distinguished from the Ni—Cd accumulator by measuring the amplitude of signal S at an excitation frequency f1 of the order of 500 Hz.

These examples show that to increase the reliability of the analysis, it is possible to combine the response curves of signal S respectively as a function of the frequency and the amplitude of the excitation voltage. It is possible in this case to include in the measuring device two or more excitation circuits 17, and to apply consecutively to these two excitation circuits two different voltage values at two different frequencies.

We claim:

1. An apparatus for sorting used batteries or accumulators comprising:
   at least one battery sorting device controlled by an output signal of a measuring device for analyzing ferromagnetic properties of the used batteries or accumulators, said measuring device comprising:
   at least one variable voltage source;
   an excitation circuit composed of at least one coil supplied by said at least one variable voltage source for producing a flux through a ferromagnetic mass of the battery or accumulator to be analyzed;
   an inductive sensor coupled with said excitation circuit; and
   treatment elements for processing electrical signals from said inductive sensor and supplying said output signal as a function of constitution and ferromagnetic mass of the battery or accumulator.

2. The apparatus of claim 1, wherein said at least one variable voltage source applies to said excitation circuit at least one of (i) two different amplitudes of voltage at the same frequency, and (ii) one amplitude of voltage at two different frequencies.

3. The apparatus of claim 2, wherein said at least one variable voltage source applies to said excitation circuit two different amplitudes of voltage at the same frequency.

4. The apparatus of claim 2, wherein said at least one variable voltage source applies to said excitation circuit one amplitude of voltage at two different frequencies.

5. The apparatus of claim 1, wherein said inductive sensor comprises at least one coil.

6. The apparatus of claim 1, wherein said inductive sensor comprises Hall-effect probes.

7. The apparatus of claim 1, wherein said treatment elements comprise at least one of (i) at least one voltage amplifier and (ii) at least one filter.

8. A process for sorting used batteries or accumulators using the apparatus of claim 1, comprising:
   applying at least one variable voltage through the excitation circuit composed of at least one coil supplied by the at least one variable voltage source for producing a flux through a ferromagnetic mass of at least one battery and accumulator;
   processing electrical signals from the inductive sensor with the treatment elements to provide the output signal as a function of constitution and ferromagnetic mass of the battery or accumulator; and
   controlling sorting of the batteries and accumulators as a function of the output signal.

9. The process of claim 8, wherein the applying at least one variable voltage comprises applying to the excitation circuit at least one of (i) two different amplitudes of voltage at the same frequency, and (ii) one amplitude of voltage at two different frequencies.

10. The process of claim 9, wherein the applying at least one variable voltage comprises applying to the excitation circuit two different amplitudes of voltage at the same frequency.

11. The process of claim 9, wherein the applying at least one variable voltage comprises applying to the excitation circuit one amplitude of voltage at two different frequencies.

12. The process of claim 8, wherein the controlling sorting comprises codifying the output signal by a computer program.

13. The process of claim 8, wherein the batteries and accumulators are selected from the group consisting of zinc-carbon batteries, alkaline batteries, mercury batteries, silver batteries, zinc-air batteries, and nickel-cadmium accumulators.

* * * * *